United States Patent [19]
Jacobs

[11] Patent Number: 5,746,772
[45] Date of Patent: May 5, 1998

[54] PROSTHETIC SOCKET

[75] Inventor: Gilbert R. Jacobs, Landing, N.J.

[73] Assignees: Ja-Bar Silicone Corp., Andover, N.J.; Ortho Europe Ltd., Oxon, United Kingdom

[21] Appl. No.: 782,123

[22] Filed: Jan. 13, 1997

[51] Int. Cl.$^6$ ................................................ A61F 2/80
[52] U.S. Cl. .................................. 623/35; 623/36
[58] Field of Search ................................ 623/32–37

[56] References Cited

U.S. PATENT DOCUMENTS

| | | | |
|---|---|---|---|
| 2,578,019 | 12/1951 | Ryan . | |
| 2,634,424 | 4/1953 | O'Gorman | 623/37 |
| 3,393,407 | 7/1968 | Kardel | 623/37 |
| 3,520,002 | 7/1970 | Wellington . | |
| 4,134,159 | 1/1979 | Wilson | 623/35 |
| 4,923,474 | 5/1990 | Klasson et al. | 623/33 |
| 5,201,774 | 4/1993 | Greene | 623/34 |
| 5,464,443 | 11/1995 | Wilson et al. | 623/37 |
| 5,480,455 | 1/1996 | Norvell | 623/36 |
| 5,507,834 | 4/1996 | Laghi | 623/36 |
| 5,593,454 | 1/1997 | Helmy | 623/32 |

OTHER PUBLICATIONS

Wilson et al, "Improvement of the Air Cushion Socket for Below–Knee Amputees", Proceeding of the 2nd International Conference on Rehabilitation Engineering, 1984, p. 239.

*Primary Examiner*—Mary Beth Jones
*Attorney, Agent, or Firm*—Thomas L. Adams

[57] ABSTRACT

A prosthetic socket is adapted to support a prosthesis and is also adapted to be worn on a stump of a partially amputated limb. This socket has a coupler for holding the prosthesis along a prosthetic axis. The socket also has a cup with an inside surface and an outside surface. This inside surface is adapted to fit on the stump. The coupler is centrally attached to the cup to face outwardly from the outside surface. The cup contains a separated plurality of contractible cavities distributed around the prosthetic axis between the inside surface and the outside surface to provide cushioning by allowing deflection of the cup along the prosthetic axis into the cavities to contract the cavities. The cup can be formed with a plurality of angularly spaced, elongate, blind holes extending away from a central location. These blind holes can be plugged to prevent intrusion of debris. In an alternative cup, a molded cap can be affixed over a molded boot, while leaving interspaces that form spaced, closed cavities.

24 Claims, 5 Drawing Sheets

5,746,772

PROSTHETIC SOCKET

FIELD OF THE INVENTION

The present invention relates to a prosthetic socket, and in particular to a socket that provides cushioning between the prosthesis and the stump of an amputated limb.

DESCRIPTION OF RELATED ART

Amputees can wear a cup-shaped socket at the distal end of a stump. This socket can be molded around a threaded fitting having a dome-shaped flange. A prothesis with a concave, proximal end can have a stud that can be threaded into this fitting. A socket supporting the prosthesis should be able to sustain the various forces exerted at varying angles during walking or other activities.

When a person loses part of a limb, usually there is very little extra skin or tissue at the stump to act as a cushion for a prosthetic device. Attempts to cushion the device by using pliable or flexible sockets have limitations. A socket should not deform to such an extent that the prosthesis feels wobbly. Maintaining an appropriate balance between comfort and stability can be difficult. A prosthetic socket should also be easily attached, allow the transference of forces during movement of the prosthetic device, and provide proper stability to prevent the socket from twisting or bending, while still feeling comfortable and offering sufficient cushioning.

In U.S. Pat. No. 2,578,019 a socket is lined with side padding and bottom padding. These pads are foam or sponge rubber material provided with ventilation holes normal to the skin. These holes are open at both ends and will tend to accumulate debris. Also, the specification of this reference suggests that these holes are for ventilation, not cushioning. The main cushioning effect would be due to compression of the padding itself. Consequently, the pads will introduce instability to the prosthesis.

U.S. Pat. No. 5,139,523 shows a socket that is fitted with an inflatable bladder that engages the distal end of a limb stump. This bladder communicates with a sidewall bladder. Both bladders can be inflated through an external valve fitting. Thus these bladders will tend to deform rapidly and destabilize the prosthesis. Also the bladders will tend to collapse rapidly on impact and this resulting bottoming will induce high impact forces into the stump.

U.S. Pat. No. 2,634,424 shows inflatable compartments that surround the circumference of a leg stump. There is no subjacent support at the distal end of the stump. Instead, a fillet on the socket engages either the knee structure or the fleshy part of the buttocks to provide vertical support.

U.S. Pat. No. 5,464,443 shows a socket with a pad for supporting the distal end of a stump. Liquid filled pouches encircle the circumference of the stump. Although the pouches appear to protrude partially under the pad, these do not appear to provide a cushioning effect for the pad. The pad instead appears to be rigidly supported by a post.

U.S. Pat. No. 3,520,002 shows an artificial limb with a socket formed of a foam material.

See also U.S. Pat. Nos. 4,923,474; 5,201,774; 5,480,455; and 5,507,834.

Accordingly, there is a need for an improved prosthetic socket that can provide both support and comfort to the user.

SUMMARY OF THE INVENTION

In accordance with the illustrative embodiments demonstrating features and advantages of the present invention, there is provided a prosthetic socket adapted to support a prosthesis and adapted to be worn on a stump of a partially amputated limb. The socket has a coupler for holding the prosthesis along a prosthetic axis. The socket also has a cup with an inside surface and an outside surface. The inside surface is adapted to fit on the stump. The coupler is centrally attached to the cup to face outwardly from the outside surface. The cup contains a separated plurality of contractible cavities distributed around the prosthetic axis between the inside surface and the outside surface to provide cushioning by allowing deflection of the cup along the prosthetic axis into the cavities to contract the cavities.

According to another aspect of the invention, there is provided a method for making a prosthetic socket that is adapted to support a prosthesis. The method includes the step of forming a cup having a plurality of angularly spaced, elongate, blind holes extending away from a central location. Another step is plugging the blind holes to prevent intrusion of debris.

According to still another aspect of the invention, there is provided a method for making another prosthetic socket also adapted to support a prosthesis. The method includes the step of molding a cap and molding a boot. Another step is affixing the cap over the boot while leaving interspaces that form spaced, closed cavities.

By employing apparatus and methods of the foregoing type, an improved prosthetic socket can be achieved, which provides stable support for the prosthesis and comfort to the user. In the preferred embodiment, the prosthetic socket fits over the distal end of a leg stump. The socket has a cup with an inside surface that engages the stump. A receiving coupler is preferably molded into the socket for attachment to the prosthesis. The cup of the socket is made of a deflectable material, which provides the required support, stability, reliability and maintainability.

The preferred socket has a plurality of cavities distributed inside the cup. In one preferred embodiment, non-intersecting, elongate holes diverge laterally from a location near the axis of the prosthesis. In that embodiment the cavities are balanced around the prosthetic axis and shaped to avoid destabilization of the prosthesis. The cup of the socket can provide cushioning when the material of the cup deflects into the cavities, causing them to contract in a direction parallel to the prosthetic axis. This arrangement of cavities is also designed to disperse the load forces over a large surface to provide better support and comfort.

In an alternate preferred embodiment, the prosthetic socket contains a plurality of compact cavities each having an essentially cylindrical shape. These cavities can be formed by attaching an elastomeric cap over a cup-shaped boot, while leaving an interspace that forms the cavities.

BRIEF DESCRIPTION OF THE DRAWINGS

The above brief description as well as other objects, features and advantages of the present invention will be more fully appreciated by the reference to the following detailed description of presently preferred, but nonetheless illustrative embodiments in accordance with the present invention, when taken in conjunction with the accompanying drawings, wherein.

3

Figure 1:
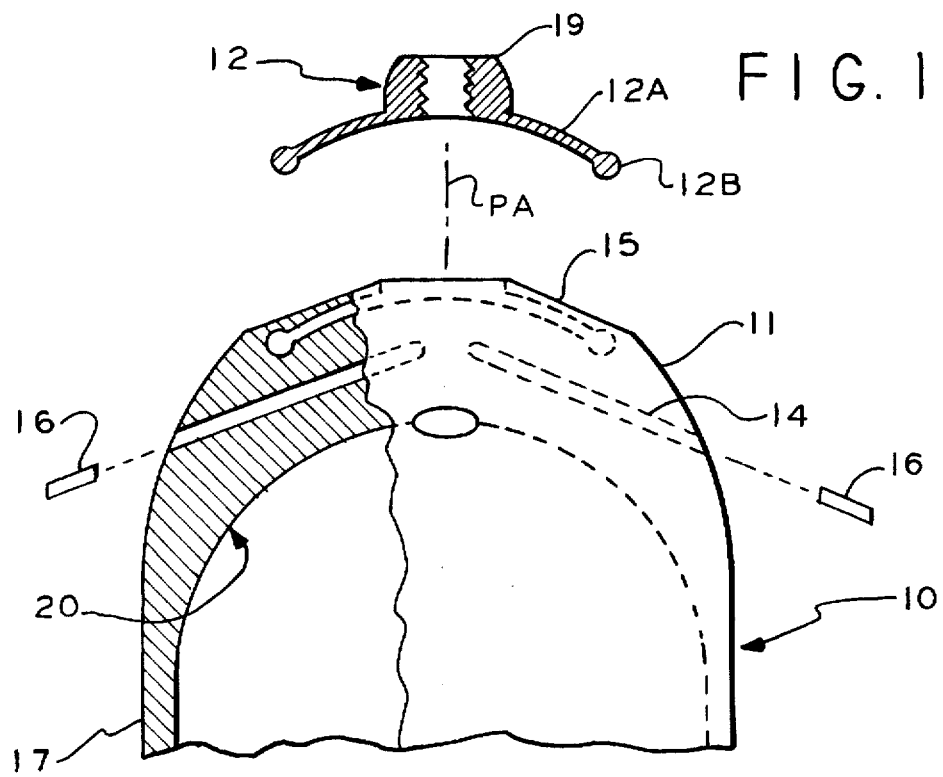
FIG. 1 is an exploded side view of a portion of a preferred prosthetic socket, showing its cup partly in section.
Figure 1A:
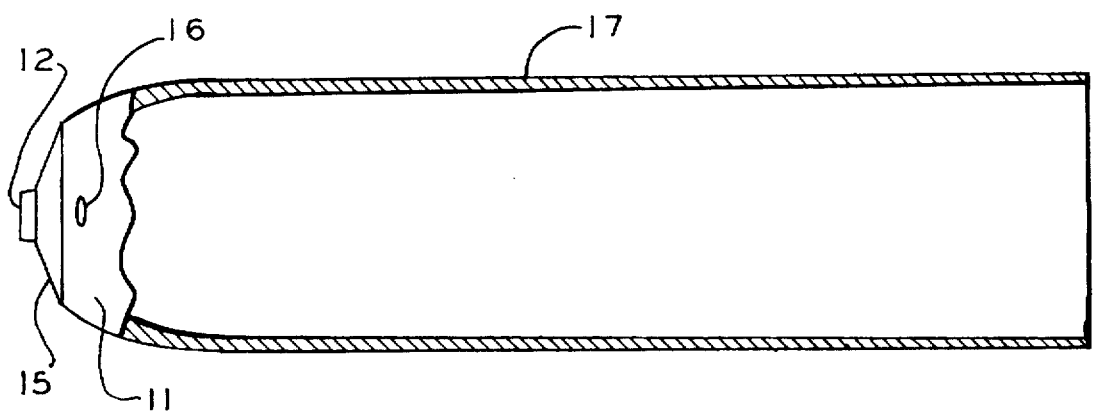
FIG. 1A is a side view of the prosthetic socket, shown in section except for the cup region.
Figure 3:
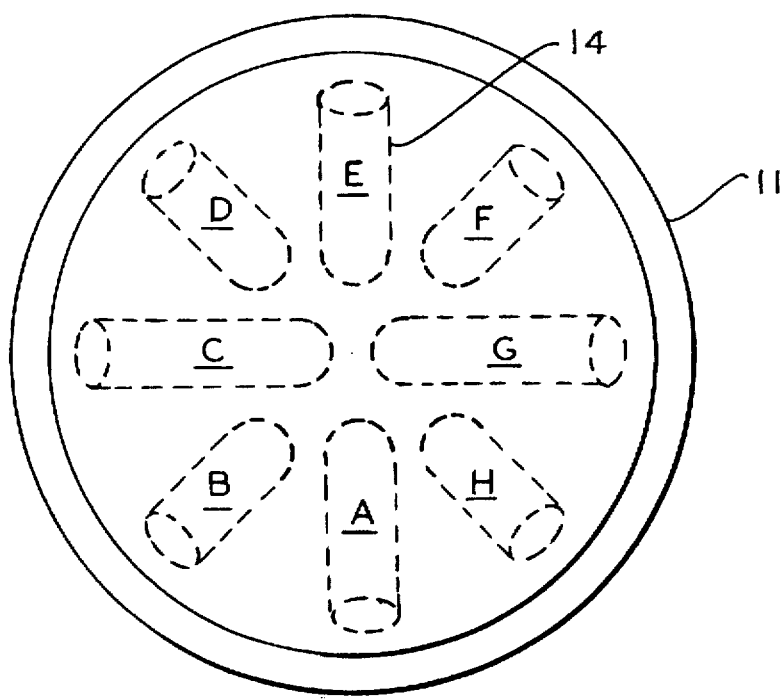

FIG. 3 is a bottom view of the preferred prosthetic socket of FIG. 1.

Figure 4:
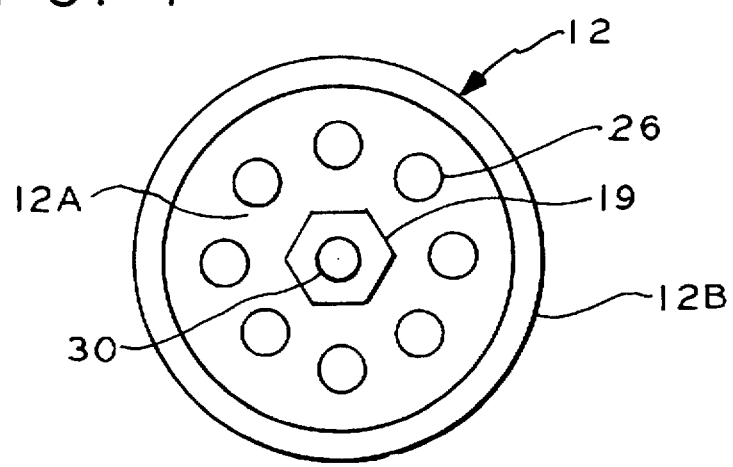

FIG. 4 is a top view of the receiving coupler of FIG. 1.

Figure 5:
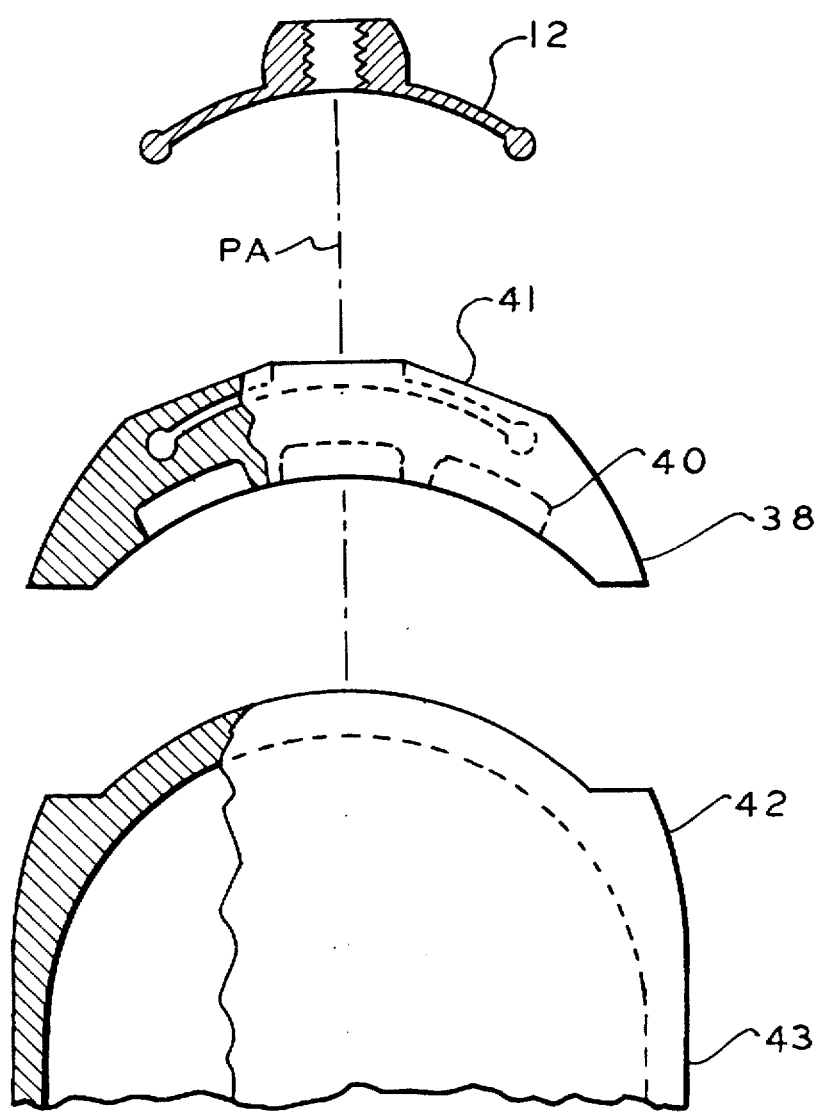

FIG. 5 is an exploded side view of a portion of an alternate preferred prosthetic socket, showing its cup formed from two parts, both shown in partial section.

Figure 6:
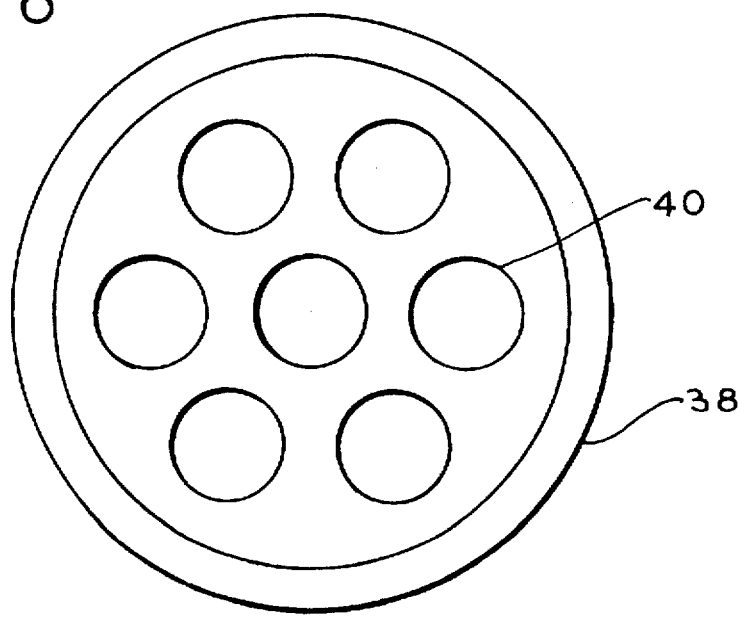

FIG. 6 is a bottom view of the cap shown in FIG. 5.

Figure 7:
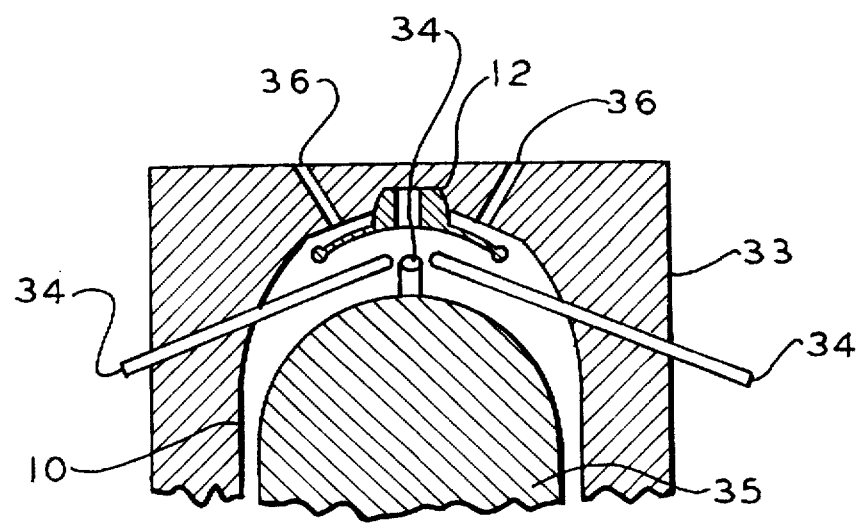

FIG. 7 is a cross-sectional view of a portion of the mold used to make the prosthetic socket of FIG. 1.

Figure 8:
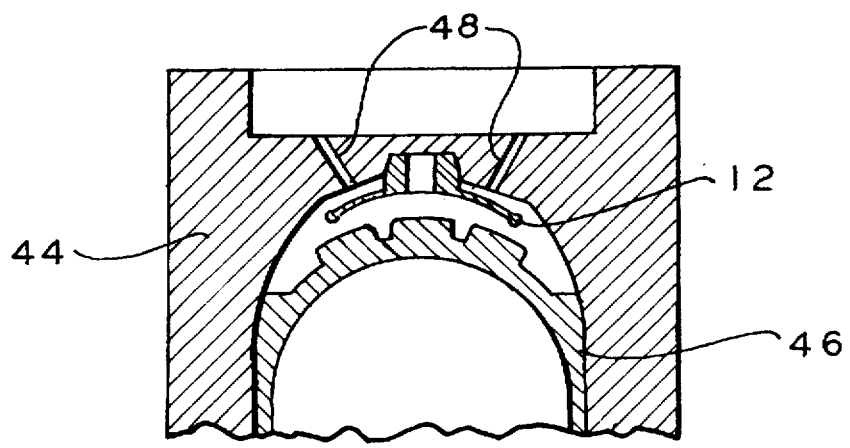

FIG. 8 is a cross-sectional view of the mold used to make the alternate preferred prosthetic socket of FIG. 5.

DETAILED DESCRIPTION OF THE PREFERRED EMBODIMENTS

Referring to FIGS. 1, 1A, 2 and 3, a prosthetic socket 10 is shown made of resilient material that is molded into a cup 11; specifically, a truncated, hollow ovoid. The outside surface 15 of the cup 11 is also ovoidal in shape to distribute forces and provide a mating surface to the curved base of prosthesis P (shown in phantom in FIG. 2).

Molded into the top of cup 11, below outside surface 15 is a metallic coupling 12 that has a dome shaped, perforated flange 12A with a beaded edge 12B. Flange 12A has a circular border and is curved to conform to the outside surface 15 of the prosthetic socket 10. The center boss 19 of the coupling 12 is a hexagonal prism with internal threads used to engage the threads of the prosthetic device P, which may be an artificial leg.

The sidewall 17 of the cup 11 is essentially cylindrical in shape and is approximately ½ inch (12.7 mm) thick, but tapers down to a thickness of 0.79 inch (2 mm). The sidewall thickness may be varied for individual comfort and strength. This preferred sidewall will have an appropriate balance between flexibility, comfort, and the strength required to support the prosthesis P.

The cylindrical sidewall 17 is approximately 13.54 inches (34.4 cm) long, with an overall length, including the cup 11 (but excluding boss 19), of 15.45 inches (39.2 cm). The specific length, however, may be varied to accommodate limbs of various lengths or to provide a different level of support, comfort, etc.

The inside surface 20 of socket 10 is tapered inwardly to form a domed shape that mates to the stump (not shown) at the distal end of the leg. This section provides support and distributes the force from the prosthesis P along most of the inside surface of the prosthetic socket 10. In some embodiments surface 20 may be lined with a curable silicone that is molded by the stump itself to provide a custom-fitted surface.

The domed base of cup 11 containing coupler 12 is thickened and is approximately 1 inch (2.5 cm) thick, but may have different thickness depending on the desired stiffness, strength, cushioning, etc. This dome shaped region contains cavities 14, which provide cushioning. In this embodiment cavities 14 are elongate cavities, but may be filed with a compressible material in other embodiments having a different hardness.

Cup 11 is shown molded with eight cavities 14 arranged in a balanced fashion around the circumference of the socket. The cavities 14 are elongate tunnels designed to provide cushioning without destabilizing the supportive structural properties of the socket 10. To prevent a buildup of moisture, debris and other contamination, the open ends of the cavities 14 are sealed with plugs 16 made of the same material and shaped to fit into the cavities. The plugs 16 are fitted flush with the outside of the socket and are bonded in place by glue, heat sealing or the like.

The cavities 14 are blind holes having an elliptical cross-section and extending outwardly to side of cup 11. Cavities 14 extend from a location near the prosthetic axis PA at an acute angle, directed slightly away from coupler 12.

As shown in FIG. 3, cavities 14 are spaced equiangularly along the outside circumference of cup 11 with a separation of 45 degrees from each other. Their size is determined by the amount of strength, cushioning and stiffness needed, in dependence on the size of the prosthesis P and the cup 11. Cavities C and G are the deepest with cavities A and E the next deepest. Cavities B, D, F and H are of equal depth and are the shallowest. The cavities are straight elliptical tunnels that penetrate at an angle of approximately 20 degrees from prosthetic axis PA, although other angles of inclination are possible depending upon the geometry of cup 11.

The thickness of the material in the vicinity of cavities 14 and coupler 12 must be sufficient to avoid tearing and prevent the coupler from being torn out of the prosthetic socket. The thickness will therefore also depend upon the size and weight of the individual using the device. The cup 11 of the prosthetic device is designed to provide the cushioning to the stump end of the leg and provide the strength required to support the prosthetic device.

The material used to form the main body of cup 11 is preferably a silicone elastomer. This material can be clear, non-toxic, easily sterilized, as well as being easily molded. In alternate embodiments, different materials can be used to provide either stiffer or softer support. For example, one may use soft vinyl, natural latex, rubber, millable gum material or other silicone polymers. Alternate materials may also be required if an allergic reaction to the elastomer occurs. Decreasing the hardness of the elastomer increases the cushioning effect, but decreases its stability and strength.

The material of the cup 11 must be sufficiently strong to avoid breaking or tearing. A silicone elastomer may have a tensile strength of about 630 psi. The total projected area of the cup 11 may be approximately 12 square inches (77 square centimeters), but the effective "load area" is in the vicinity of 7 square inches (45 square centimeters), encompassing approximately a 3 inch (7.6 cm) diameter. The cavities reduce the effective load area across the elastomer by about 50%. This yields a net tensile strength of about 3,800 pounds (1727 kg), although other tensile strengths may be designed into other embodiments.

The elastomer should be essentially non-compressible. Still, each time a force is applied some deformation will occur and the elastomer will bend or deflect before returning to its original shape. The hardness (durometer) of the elastomer will be selected to strike a balance between stability and comfort. The design will also be affected by the strength of the material used, its resiliency, as well as the affect on resiliency and strength caused by the location and size of the cavities.

Referring to FIGS. 1 and 4, previously mentioned coupler 12 is shown having a circular outline. The rim 12B of the coupler is beaded to increase strength and rigidity without excessively increasing its weight or size. The flange portion 12A is domed between boss 19 and rim 12A to better conform to the outside surface of the prosthetic socket 10. The coupler 12 has a diameter of approximately 2 5/16 inch (5.9 cm), but can be varied depending upon the size of the prosthetic socket 10.

The flange portion 12A of the coupler contains eight, equiangularly spaced holes 26, approximately ⅛ inch (3.2 mm) in diameter, but can be of different diameters depending upon the application. The holes allow the material of the cup 11 to infiltrate and integrate with the coupler 12 to prevent the coupler 12 from rotating or being otherwise dislodged from its location. Boss 19 of coupler 12 is approximately ½ inch (1.3 cm) tall, but can be varied if required to fit the prosthesis. The coupler 12 has the shape of a hexagonal prism with an internally threaded center bore 30. The internal threads are designed to accept attachment of the prosthesis.

Figure 2:
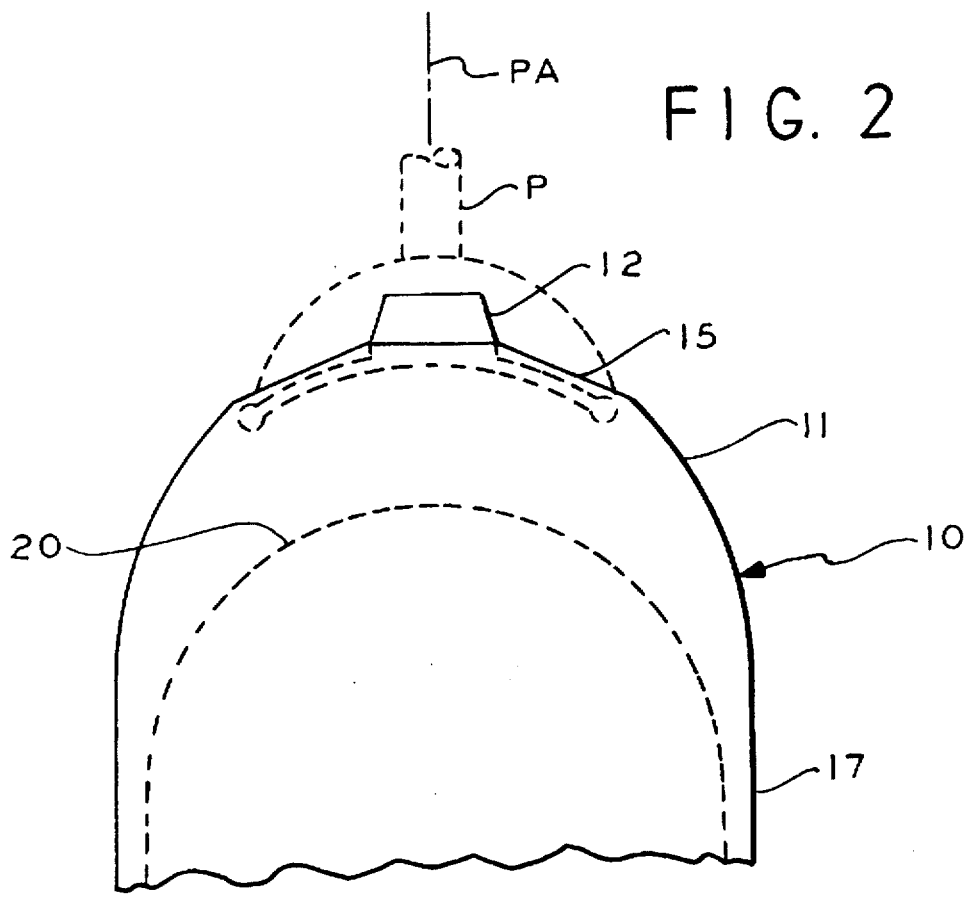
FIG. 2 is a non-exploded, side view of a portion of the preferred prosthetic socket of FIG. 1.

Referring to FIG. 7, a mold is shown for making the socket shown in FIGS. 1 through 3. The mold is made of an upper portion 33 with a concave molding surface and a lower portion 35 with a convex molding surface. Rods 34 having an elliptical cross section are inserted transversely through the mold section 34 to the desired depth to obtain the correct cavity configuration. The minor transverse axes of the rods 34 are directed axially. The coupler 12 is secured to the top of the mold section 33 before the mold sections 33 and 35 are closed. Elastomer is then injected through holes 36 of the mold and allowed to harden or cure. The rods 34 are then removed and the sections 33 and 35 separated to allow removal of the prosthetic socket.

In the alternate preferred embodiment shown in FIGS. 5 and 6, the prosthetic socket has three distinct components. Upper portion 38 is a domed, molded cap having on its concave underside seven blind holes 40 that ultimately form internal cylindrical cavities in the finished unit. The convex outside surface 41 of cap 38 is shaped to distribute the forces and to provide a mating surface to the prosthesis.

The cavities 40 are approximately ¾ inch (19 cm) in diameter and approximately ¼ inch (6.35 cm) high, but can have different dimensions to provide different strength, stability and cushioning effects. Cavities 40 are arranged with one concentric hole surrounded by six equiangularly spaced holes as shown in FIG. 5. The holes are spaced far enough apart to avoid tearing or cracking that would reduce the life of the socket.

Cap 38 also contains the coupler 12 previously shown in FIG. 4. Coupler 12 is embedded by being molded into cap 38.

The third or bottom portion 42 is a cup-shaped boot. Boot 42 may be made of the same material as cap 38, although in other embodiments boot 38 may be made of a different material with a different durometer. The sidewall 43 of the boot 42 is essentially cylindrical in shape and has a flexibility and strength required to support the prosthesis. Boot 42 has a domed base shaped to mate with cap 38. The two pieces 38 and 42 are bonded together to form a sealed unit by gluing, heat sealing or the like. The joint may be colored by a pigment for cosmetic reasons. When so joined the underside of cap 38 is sealed to close the openings of its cavities 40.

The cavities thus formed in this and other embodiments can have a volume providing a desired level of strength and cushioning, as well as a reduction in overall weight. Besides the configurations just described, alternate cavities can be arranged in a set of concentric arcs, segmented to form independent cavities. The arcs may be isolated from each other to keep a balanced presence of solid material around the prosthetic axis PA to enhance stability. In some embodiments the cup can have more than two layers and every interface between the layers can have cavities. In addition, the cavities can be fully or partially filled with different materials (solid, liquid compressible, etc.) to vary the quality of the cushioning and stability. The arrangement of the cavities and their size must be balanced with the material properties to provide the durability required of the prosthetic socket.

Referring to FIG. 8, a mold is shown for making cap 38 of the prosthetic socket shown in FIGS. 5 and 6. The mold sections 44 and 46 produce the cavities used for cushioning. The lower section 46 of the mold has embossments for forming these cavities. The coupler 12 is attached to the roof of the upper section 44 of the mold. The mold is closed before elastomer is injected through holes 48. After the elastomer hardens, the mold is separated and the molded cap removed. The boot 42 is molded in a similar manner.

To facilitate an understanding of the principles associated with the foregoing, the use of the embodiment of FIGS. 1 through 4 will be described for a leg prosthesis. It will be appreciated that the operation of other embodiments will be similar.

A spray lubricant may be applied to the surface of socket 10 shown in FIG. 2. This allows the socket to be easily rolled and placed onto the stump of the amputee. The sidewall 17 of the socket is rolled up to expose as much as possible of the inside surface 20 of cup 11. The surface 20 is then placed securely against the stump and the socket sidewall 17 is rolled back over the limb. The alignment of the coupler 12 is important, as the prosthesis P must transfer forces to coupler 12 without inducing lateral strain. The prosthetic device P is then screwed into coupler 12.

When walking, each step produces a variety of forces on the prosthetic socket 10 that form a cycle of compression and relaxation. As a step is taken the force from the heel of the foot is applied along the axial length of the prosthesis P, which is then transferred to the prosthetic socket. This force may be applied at an angle to prosthetic axis PA. As the pressure on the foot is transferred from the heel to the ball of the foot, the net force applied to the socket 10 may shift angularly. This produces a changing force that tends to deflect or deform the socket.

During the use of the prosthetic socket, forces are applied to the device in a cyclic fashion each time a step is taken. The forces will be applied to the top surface of cup 11 primarily through coupler 12. Since the forces are not applied equally along the surface they tend to deform cup 11. The device must be designed to withstand these forces and still provide cushioning to reduce the pressure on the stump.

In response to these forces, the cavities 14 will contract and therefore absorb some of the applied forces. The elastomer material is relatively noncompressible but the cavities 14 produce some cushioning without destabilizing the prosthesis P. The walking forces tend to spread from the center of the prosthetic axis PA and tend to deflect the solid material of cup 11. In effect, the cavities 14 contract in a direction parallel to prosthetic axis PA as the material of cup 11 deflects. This deflection favors resilience along the prosthetic axis PA but without a significant tendency for the prosthesis P to wobble (angularly deflect relative to the leg). The cavities 14 are placed in a balanced pattern around the socket to allow deflection of the material of cup 11 into the cavities 14 without a specific bias.

Although the total projected area of the cup 11 is approximately 12 square inches (77 square centimeters), the "load area" is in the vicinity of 7 square inches (45 square centimeters), encompassing approximately a 3 inch (7.6 cm) diameter. Consequently, compression deflection into the cavities 14 can approach 0.25 inch on each cycle for cushioning the limb on each step Since the cavities 14 are sealed and separated from each other, they act as individual pistons to provide cushioning and balanced stability to the socket. This also disperses the walking forces transferred by the socket to the stump, while producing a cushioning effect on the stump. Also, the cavities 14 are sized to stay uncollapsed during normal walking. The opposing inside surfaces of the cavities 14 are sufficiently separated to avoid touching or bottoming during normal use. Such bottoming would produce a hard feeling or shock to the stump.

Obviously, many modifications and variations of the present invention are possible in light of the above teachings. It is therefore to be understood that within the scope of the appended claims, the invention may be practiced otherwise than as specifically described.

I claim:

1. A prosthetic socket adapted to support a prosthesis and adapted to be worn on a stump of a partially amputated limb, comprising:

a coupler for holding said prosthesis along a prosthetic axis;

a cup having an inside surface an d an outside surface, said inside surface being adapted to fit on said stump, said coupler being centrally attached to said cup to face outwardly from said outside surface, said cup containing a separated plurality of contractible cavities distributed around said prosthetic axis between said inside surface and said outside surface to provide cushioning by allowing deflection of said cup into said cavities along said prosthetic axis to contract said cavities.

2. A prosthetic socket according to claim 1 wherein said cavities are balanced about said prosthetic axis.

3. A prosthetic socket according to claim 1 wherein at least one of said cavities is located at said prosthetic axis.

4. A prosthetic socket according to claim 1 wherein said cavities are sized to allow contraction without bottoming in response to routine force applied along said prosthetic axis.

5. A prosthetic socket according to claim 1 wherein said cup is comprised of a deflectable material, said cup providing the cushioning more by deflecting than compressing the deflectable material.

6. A prosthetic socket according to claim 5 wherein said deflectable material of said cup is substantially non-compressible.

7. A prosthetic socket according to claim 1 wherein said cavities comprise:

a plurality of angularly spaced tunnels extending away from said prosthetic axis.

8. A prosthetic socket according to claim 7 wherein said tunnels extend away from the prosthetic axis at an acute angle thereto.

9. A prosthetic socket according to claim 8 wherein said tunnels are non-intersecting, are distributed conically, and are spaced equiangularly.

10. A prosthetic socket according to claim 8 wherein at least one of the tunnels is longer than another one of the tunnels.

11. A prosthetic socket according to claim 7 wherein said cavities comprise a plurality of blind holes, said socket comprising:

a plurality of plugs separately fitted into corresponding ones of said blind holes to close them.

12. A prosthetic socket according to claim 1 wherein said cavities are closed.

13. A prosthetic socket according to claim 12 wherein a central one of said cavities is aligned with said prosthetic axis.

14. A prosthetic socket according to claim 13 wherein some of said cavities are spaced from said prosthetic axis and said central one of said cavities.

15. A prosthetic socket according to claim 12 wherein some of said cavities are distributed around said prosthetic axis with equiangular spacing.

16. A prosthetic socket according to claim 12 wherein said cup comprises:

an inner boot; and an outer cap affixed upon said inner boot, said cavities being formed by interspacing between said boot and said cap.

17. A prosthetic socket according to claim 16 wherein said inner boot is molded and said outer cap is glued to said boot.

18. A prosthetic socket according to claim 1 wherein said cup is molded.

19. A prosthetic socket according to claim 1 wherein said cup is elastomeric.

20. A prosthetic socket according to claim 19 wherein said cup comprises a molded silicone.

21. A prosthetic socket according to claim 19 wherein said cup is translucent.

22. A prosthetic socket according to claim 19 wherein said cup is transparent.

23. A prosthetic socket according to claim 19 wherein said coupler comprises:

a flange embedded in said cup; and an internally threaded boss affixed to said flange and extending out of said cup for receiving said prosthesis.

24. A prosthetic socket according to claim 23 wherein said flange is dome shaped and the outside surface of said cup is convex.

* * * * *